US007279169B1

(12) United States Patent
Rappuoli et al.

(10) Patent No.: US 7,279,169 B1
(45) Date of Patent: Oct. 9, 2007

(54) MUCOSAL DTPA VACCINES

(75) Inventors: Rino Rappuoli, Siena (IT);
Mariagrazia Pizza, Siena (IT)

(73) Assignee: Novartis Vaccines and Diagnostics SRL, Siena (IT)

( * ) Notice: Subject to any disclaimer, the term of this patent is extended or adjusted under 35 U.S.C. 154(b) by 475 days.

(21) Appl. No.: 10/089,367

(22) PCT Filed: Sep. 28, 2000

(86) PCT No.: PCT/IB00/01440

§ 371 (c)(1),
(2), (4) Date: Dec. 27, 2002

(87) PCT Pub. No.: WO01/22993

PCT Pub. Date: Apr. 5, 2001

(30) Foreign Application Priority Data

Sep. 29, 1999 (GB) .................................. 9923060.9

(51) Int. Cl.
*A61K 39/02* (2006.01)
*A61K 39/05* (2006.01)
*A61K 39/116* (2006.01)
*A61K 39/10* (2006.01)
*A61K 39/08* (2006.01)
*A61K 38/00* (2006.01)
*C07K 1/00* (2006.01)

(52) U.S. Cl. .............................. 424/236.1; 424/234.1; 424/203.1; 424/184.1; 424/245.1; 424/247.1; 424/242.1; 424/240.1; 424/239.1; 424/254.1; 424/238.1; 424/197.11; 424/832; 514/2; 530/350; 530/825

(58) Field of Classification Search ........... 424/197.11, 424/234.1, 236.1, 184.1, 238.1, 239.1, 240.1, 424/242.1, 247.1, 254.1, 832; 514/2; 530/825, 530/350
See application file for complete search history.

(56) References Cited

U.S. PATENT DOCUMENTS

| 5,182,109 | A | | 1/1993 | Tamura et al. ................ 424/92 |
| 5,614,382 | A | * | 3/1997 | Metcalf ...................... 435/69.1 |
| 6,562,352 | B1 | * | 5/2003 | Roberts et al. ........... 424/240.1 |
| 7,115,730 | B1 | * | 10/2006 | Pizza et al. ................ 536/23.7 |

FOREIGN PATENT DOCUMENTS

| EP | 0462534 A2 | 12/1991 |
| WO | WO 93/13202 A1 | 7/1993 |
| WO | WO 93/21950 A1 | 11/1993 |
| WO | WO 93/24148 A1 | 12/1993 |
| WO | WO 97/02348 A1 | 1/1997 |
| WO | WO 98/18298 A1 | 4/1998 |

OTHER PUBLICATIONS

Ann. lg. 79-84, 1991.*
Almeida & Alpar, "Nasal Delivery of Vaccines",*J. Drug Targeting* 3: 455-467.
Cahill et al., "Immune responses and protection against *Bordetella pertussis* infection after intranasal immunization of mice with filamentous haemagglutinin in solution or incorporated in biodegradable microparticles," *Vaccine* 13:455-462, 1995.
Cahill et al., "Mice are protected against *Bordetella pertussis* infection by intra-nasal immunization with filamentous haemagglutinin," *FEMS Microbiology Letters* 107: 211-216, 1993.
Center for Disease Control and Prevention, "Pertussis Vaccination: Use of Acellular Pertussis Vaccines Among InfaNTS AND young Children-recommendations of the Advisory Committee on Immunization Practices (ACIP)", *Morbid. Mortal. Weekly Rep. 46*(RR-7): 1-25, 1997.
Del Giudice et al., "Molecular basis of vaccination," *Molecular Aspects of Medicine 19*: 1-70, 1998.
Douce et al., "Mutants of *Escherichia coli* heat-labile toxin lacking ADP-ribosyltransferase activity act as nontoxic, mucosal adjuvants," *PNAS USA 92*: 1644-1648, 1995.
Fontana et al., "Construction of nontoxic derivatives of cholera toxin and characterization of the immunological response against the A subunit," *Infect. Immun. 63*: 2356-2360, 1995.
Gustafsson et al., "A controlled trial of a two-component acellular, a five-component acellular, and a whole-cell pertussis vaccine," *N.. Engl. J. Med. 334*: 349-355, 1996.
Guzman et al., "Antibody responses in the serum and respiratory tract of mice following oral vaccination with liposomes coated with filamentous hemagglutinin and pertussis toxoid," *Infect. Immun. 61*: 573-579, 1993.
Hauser et al., "Development and efficacy assessment of combination vaccines, with emphasis on acellular pertussis," *Dev. Biol. Stand. 95*: 251-255, 1998.
Jones et al., "Orally administered microencapsulated *Bordetella pertussis* fimbriae protect mice from *B. pertussis* respiratory infection," *Infect. Immun. 64*: 489-494, 1996.
Mills et al., "A murine model in which protection correlates with pertussis vaccine efficacy in children reveals complementary roles for humoral and cell-mediated immunity in protection against *Bordetella pertussis*," *Infect. Immun. 66*: 94-602, 1998.
Park et al., "The mucosal adjuvanticity of two nontoxic mutants of *Escherichia coli* heat-labile enterotoxin varies with immunization routes." *Exp. Mol. Med. 32*: 72-78, 2000.

(Continued)

*Primary Examiner*—S. Devi
(74) *Attorney, Agent, or Firm*—Helen Lee; Roberta L. Robins

(57) ABSTRACT

Mucosal DTPa vaccines, especially intranasal vaccines, comprising (a) a diphtheria antigen, a tetanus antigen and an acellular pertussis antigen, and (b) a detoxified mutant of cholera toxin (CT) or *E. coli* heat labile toxin (LT). Component (b) acts as a mucosal adjuvant. The acellular pertussis antigen preferably comprises pertussis holotoxin (PT) and filamentous haemagglutinin (FHA) and, optionally, pertactin. The mucosally-delivered combined DTPa formulation is capable of generating a level of protection against *B. pertussis* infection equivalent to that observed by alum-adjuvanted parenteral administration.

9 Claims, 15 Drawing Sheets

OTHER PUBLICATIONS

Podda et al., "Phase I clinical trial of an acellular pertussis vaccine composed of genetically detoxified pertussis toxin combined with FHA and 69 kDa," *Vaccine 9*: 741-745, 1991.

Rappuoli et al., "Towards third-generation whooping cough vaccines", *Trends in biotechnology 9*: 232-238, 1991.

Rapuoli, "Rational design of vaccines," *Nature Medicine 3*: 374-376, 1997.

Ryan et al., "The adjuvant action of mutants of the heat labile toxin of *E. coli* for a nasally delivered acellular pertussis vaccine," *Immunology Letters 69*: 59, 1999.

Ryan et al., "Mutants of *Escherichia coli* heat-labile toxin act as effective mucosal adjuvants for nasal delivery of an acellular pertussis vaccine: differential effects of the nontoxic AB complex and enzyme activity on Th1 and Th2 cells," *Infection and Immunity 67*: 6270-6280, 1999.

Shahin et al., "Mucosal immunization with filamentous hemagglutinin protects against *Bordetella pertussis* respiratory infection," *Infect. Immun. 60*: 1482-1488, 1992.

Shahin et al., "Adjuvanticity and protective immunity elicited by *Bordetella pertussis* antigens encapsulated in poly(DL-lactide-co-glycolide) microspheres," *Infect. Immun. 63*: 1195-1200, 1995.

Walker, "New strategies for using mucosal vaccination to achieve more effective immunization," *Vaccine 12*: 387-400, 1994.

* cited by examiner

FIGURE 3
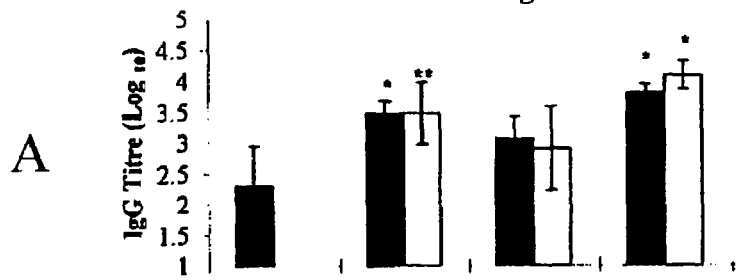
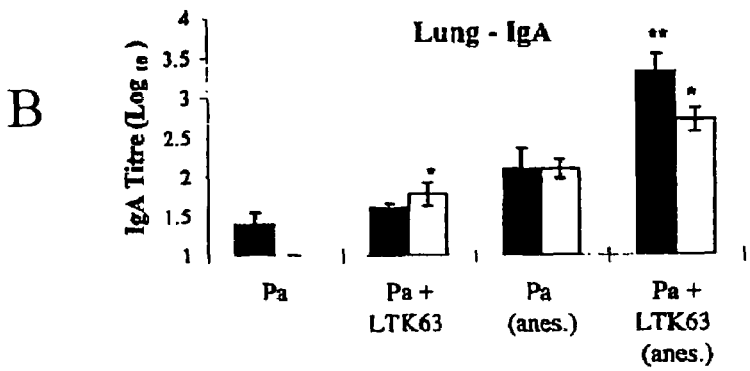
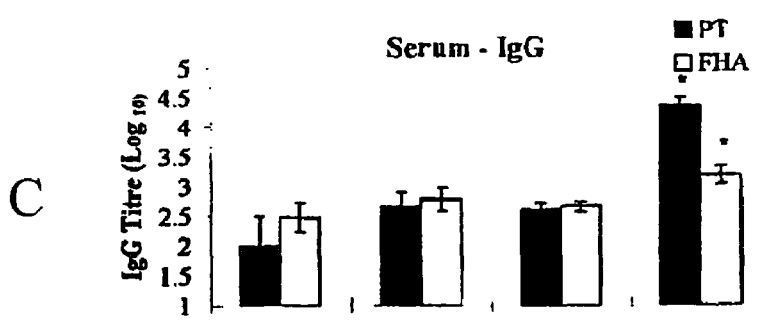
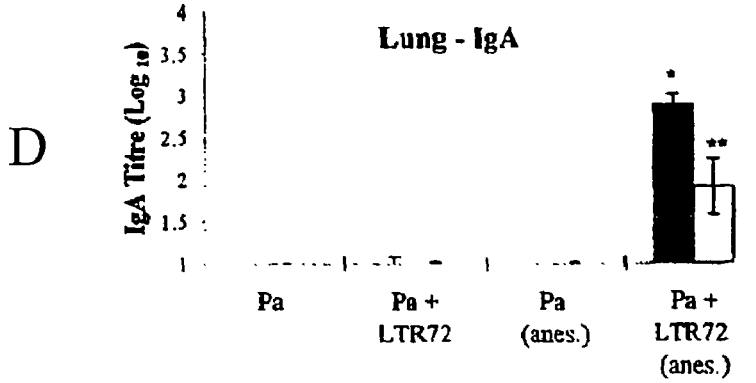

FIGURE 13
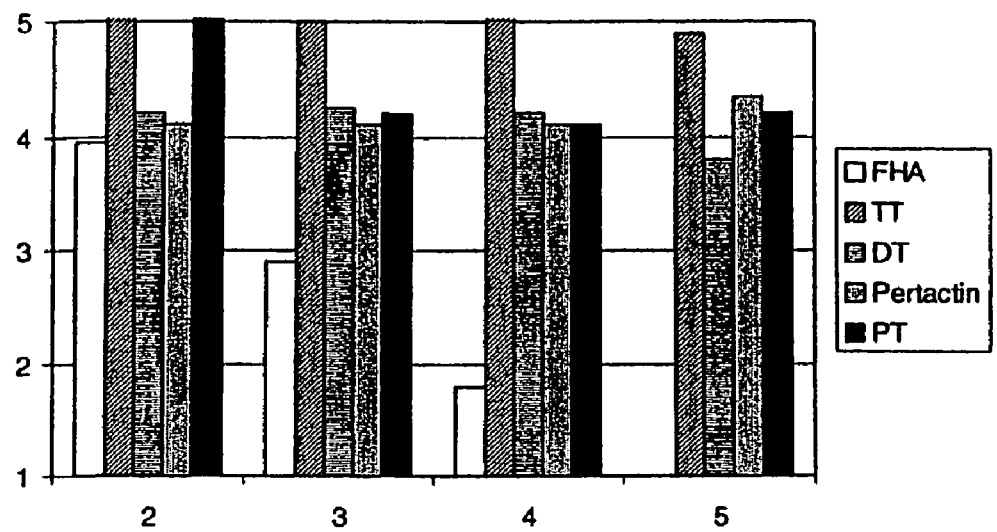
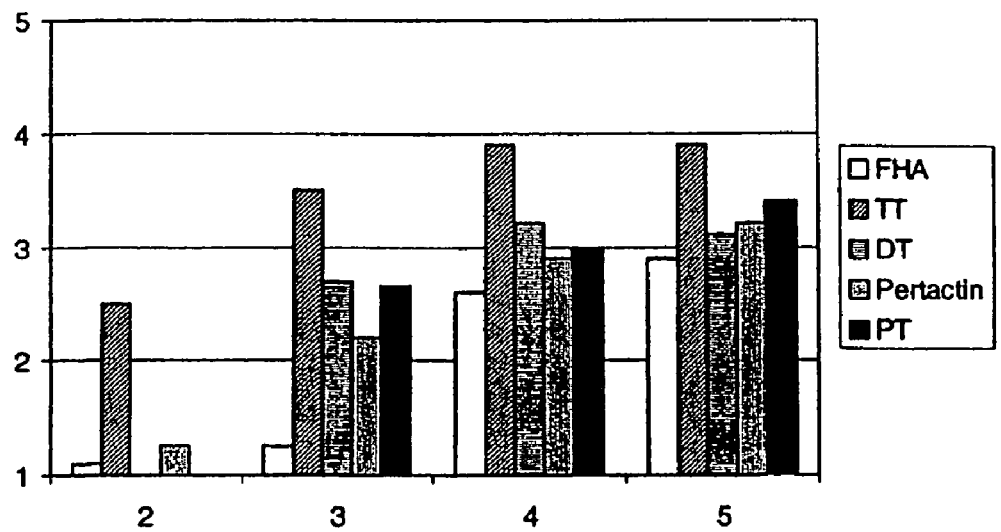

MUCOSAL DTPA VACCINES

FIELD OF THE INVENTION

This application relates to mucosal DTP vaccines, especially intranasal vaccines.

BACKGROUND TO THE INVENTION

*Bordetella pertussis* is the causative agent of whooping cough. A highly effective inactivated whole cell vaccine has been available since the 1940s but concern over its safety, due to the presence of toxic cellular components, has limited its uptake [1]. Acellular pertussis vaccines(Pa) comprising a small number of defined *B. pertussis* antigens have therefore been produced, and have been approved for use in humans [2].

Pertussis vaccines are usually administered intramuscularly to children in the form of atrivalent DTP combination (diphtheria, tetanus, pertussis) on alum adjuvant. Intramuscular vaccination is not, however, the ideal route of administration. Mucosal vaccines (oral, intranasal etc.) are preferred for two reasons [3]. Firstly, they are easier to administer on a large scale, avoiding the need for specialized equipment and the problems associated with needles. Secondly, they stimulate mucosal immunity, mediated by secretory IgA. As most pathogens enter the body across mucous membranes, mucosal immunity is desirable.

Attempts to make acellular mucosal pertussis vaccines have been described [e.g. 4,5,6,7,8,9], but the levels of protection reported were either not compared with conventional vaccine, or did not approach that observed the alum-adjuvanted antigens given parenterally.

There is therefore a need for an effective mucosal DTP combination vaccine.

DISCLOSURE OF THE INVENTION

The invention provides a mucosal DTPa vaccine comprising (a) a diphtheria antigen (D), a tetanus antigen (T), an acellular pertussis antigen (Pa), and (b) a detoxified form of either cholera toxin (CT) or *E. coli* heat labile toxin (LT).

The detoxified form of cholera toxin (CT) or *E. coli* heat labile toxin (LT) acts as a mucosal adjuvant [10]. CT and LT are homologous and are typically interchangeable. Detoxification of the CT or LT may be by chemical or, preferably, by genetic means. Suitable examples include LT having a lysine residue at amino acid 63 ["LT-K63"—ref. 11], and LT having an arginine residue at amino acid 72 ["LT-R72"—ref. 12], both of which have been found to enhance antigen-specific serum IgG, sIgA, and local and systemic T cell responses to DTPa, LT-K63 is preferred, as this has been found in a reliable animal model of *B. pertussis* infection to result in a high level of protection, equivalent to that generated with a parenterally-delivered DTPa vaccine formulated with alum. Other suitable mutants include LT with a tyrosine at residue 63 ["Y63"—ref. 13] and the various mutants disclosed in reference 14, namely D53, K97, K104 and S106, as well as combinations thereof (e.g. LT with both a D53 and a K63 mutation).

The mucosal vaccine of the invention is preferably an intranasal vaccine. In such an embodiment, it is preferably adapted for intranasal administration, such as by nasal spray, nasal drops, gel or powder [e.g. 15].

The acellular pertussis antigen preferably comprises pertussis holotoxin (PT) and filamentous haemagglutinin (FHA). It may further comprise pertactin and, optionally, agglutinogens 2 and 3 [16, 17].

PT is a toxic protein and, when present in the pertussis antigen, it is preferably detoxified. Detoxification may be by chemical and/or genetic means. A preferred detoxified mutant is the 9K/129G double mutant [2], referred to herein as "rPT".

The diphtheria antigen (D) is preferably a diphtheria toxoid, more preferably the CRM197 mutant [10]. The tetanus antigen (T) is preferably a tetanus toxoid [18].

Non-DTP antigens, preferably ones that do not diminish the immune response against the DTP components, may also be included [e.g. ref. 19, which includes a HBV antigen, and ref. 20].

The invention also provides a method of raising an immune response in a patient, comprising administering to a patient a vaccine according to the invention. The immune response is preferably protective against whooping cough, diphtheria and tetanus. The patient is preferably a child.

The method may raise a booster response, in a patient that has already been primed against *B. pertussis*. The primer vaccination may have been by a mucosal or parenteral route.

The invention also provides the use of a detoxified mutant of cholera toxin (CT) or *E. coli* heat labile toxin (LT) in the manufacture of an intranasal medicament for vaccinating a patient against whooping cough, diphtheria and tetanus, or for boosting an primer immune response previously raised against *B. pertussis*.

The invention also provides an immunogenic composition comprising (a) a diphtheria antigen (D), a tetanus antigen (T), an acellular pertussis antigen (Pa), and (b) a detoxified form of either cholera toxin (CT) or *E. coli* heat labile toxin (LT).

It will be appreciated that references in the above text to particular proteins (e.g. pertactin, PT, etc.) encompass their allelic variants and functional mutants. They also encompass proteins having significant sequence identity to the wild-type proteins. The degree of identity is preferably greater than 50% (e.g. 65%, 80%, 90%, or more) calculated using, for instance, the Smith-Waterman homology search algorithm as implemented in the MPSRCH program(Oxford Molecular), using an affine gap search with parameters gap open penalty=12 and gap extension penalty=1. Immunogenic fragments of these proteins may also be used, as may longer proteins incorporating the proteins, variants or fragments (e.g. fusion proteins). In all cases, however, the protein (whether wild-type, variant, mutant, fragment or fusion) will substantially retain the wild-type immunogenicity.

The proteins can, of course, be prepared by various means (e.g. recombinant expression, purification from cell culture, chemical synthesis etc.) and in various forms (e.g. native, fusions etc.). They are preferably prepared in substantially pure or isolated form (i.e. substantially free from other bacterial or host cell proteins with which they are normally associated in nature).

The vaccines of the invention may comprise nucleic acid for "genetic immunization" [e.g. 21]. The nucleic acid will encode a protein component of the vaccine and may replace individual protein components, or may supplement them. As an example, the vaccine may comprise DNA that encodes a tetanus toxin.

Vaccines according to the invention will typically be prophylacetic (i.e. to prevent infection), but may also be therapeutic (i.e. to treat disease after infection).

The vaccines of the invention will, in addition to components (a) and (b), typically comprise "pharmaceutically acceptable carriers," which include any carrier that does not itself induce the production of antibodies harmful to the individual receiving the composition. Suitable carriers are typically large, slowly metabolized macromolecules such as proteins, polysaccharides, polylacetic acids, polyglycolic acids, polymeric amino acids, amino acid copolymers, lipid aggregates (such as oil droplets or liposomes), and inactive virus particles. Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present.

Immunogenic compositions used as vaccines comprise an immunologically effective amount of antigen, as well as any other of the above-mentioned components, as needed. By "immunologically effective amount," it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule. The vaccine may be administered in conjunction with other immunoregulatory agents.

BRIEF DESCRIPTION OF THE DRAWINGS

FIGS. 3A-3D show antibody responses for the same vaccines. FIGS. 3A and 3B show results using LT-K63 adjuvant, and 3C and 3D show results using LT-R72 adjuvant. Filled bars show anti-PT responses; empty bars show anti-FHA responses.

FIGS. 13A-13B show serum IgG (13A) and lung homogenate IgA (13B) titres (log10) in response to the five defined antigens in the DTPa mixture.

Figure 1:
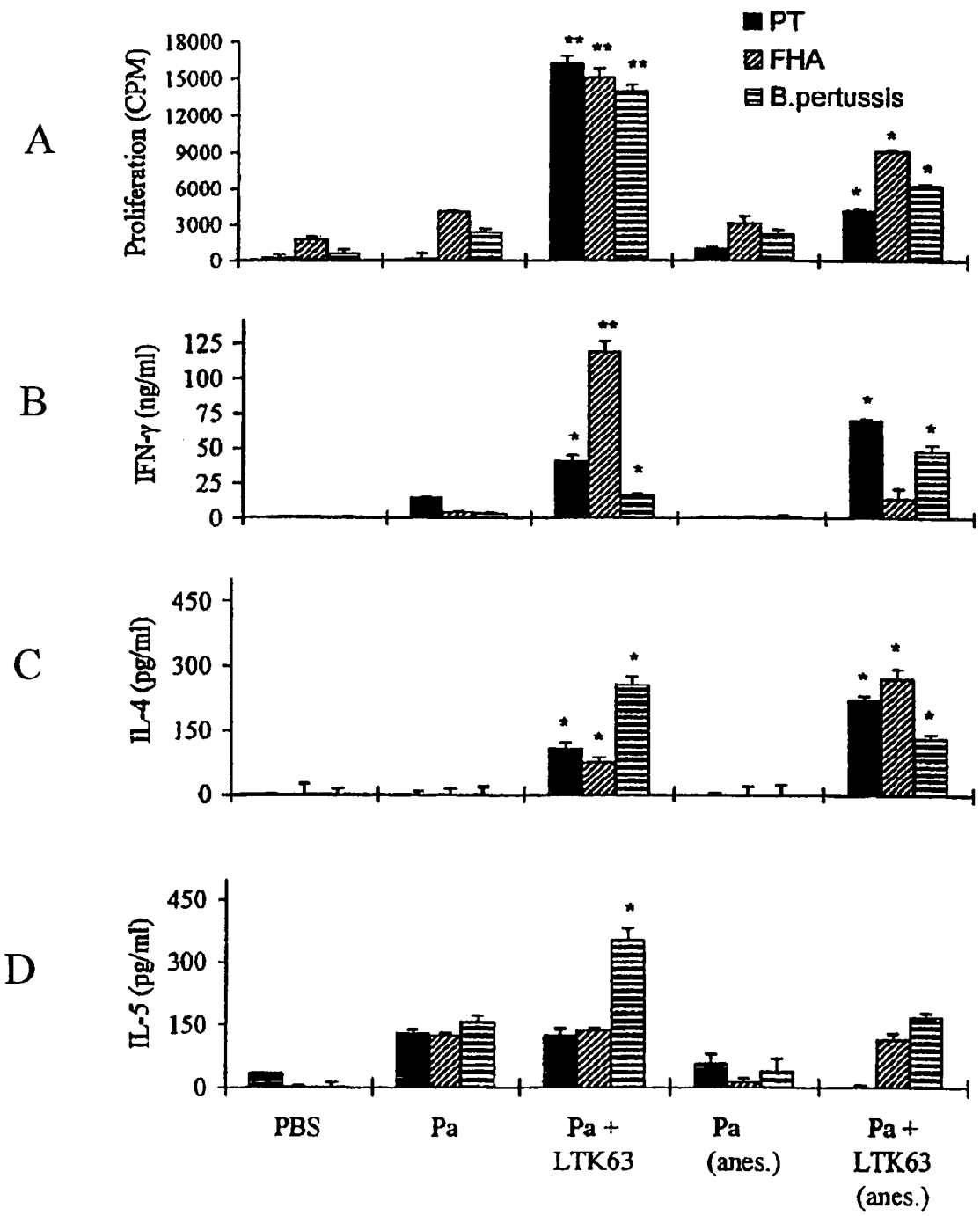
FIGS. 1A-1D show T-cell responses in spleen to an intranasal Pa vaccine adjuvanted with LT-K63. The T-cell stimulus used in the assay was: PT (filled), FHA (diagonal shading), or *B. pertussis* bacteria (horizontal lines). Pa vaccine (FHA+rPT) was delivered with or without LT-K63 adjuvant, with or without light halothane anaesthesia. PBS was a control.
Figure 2:
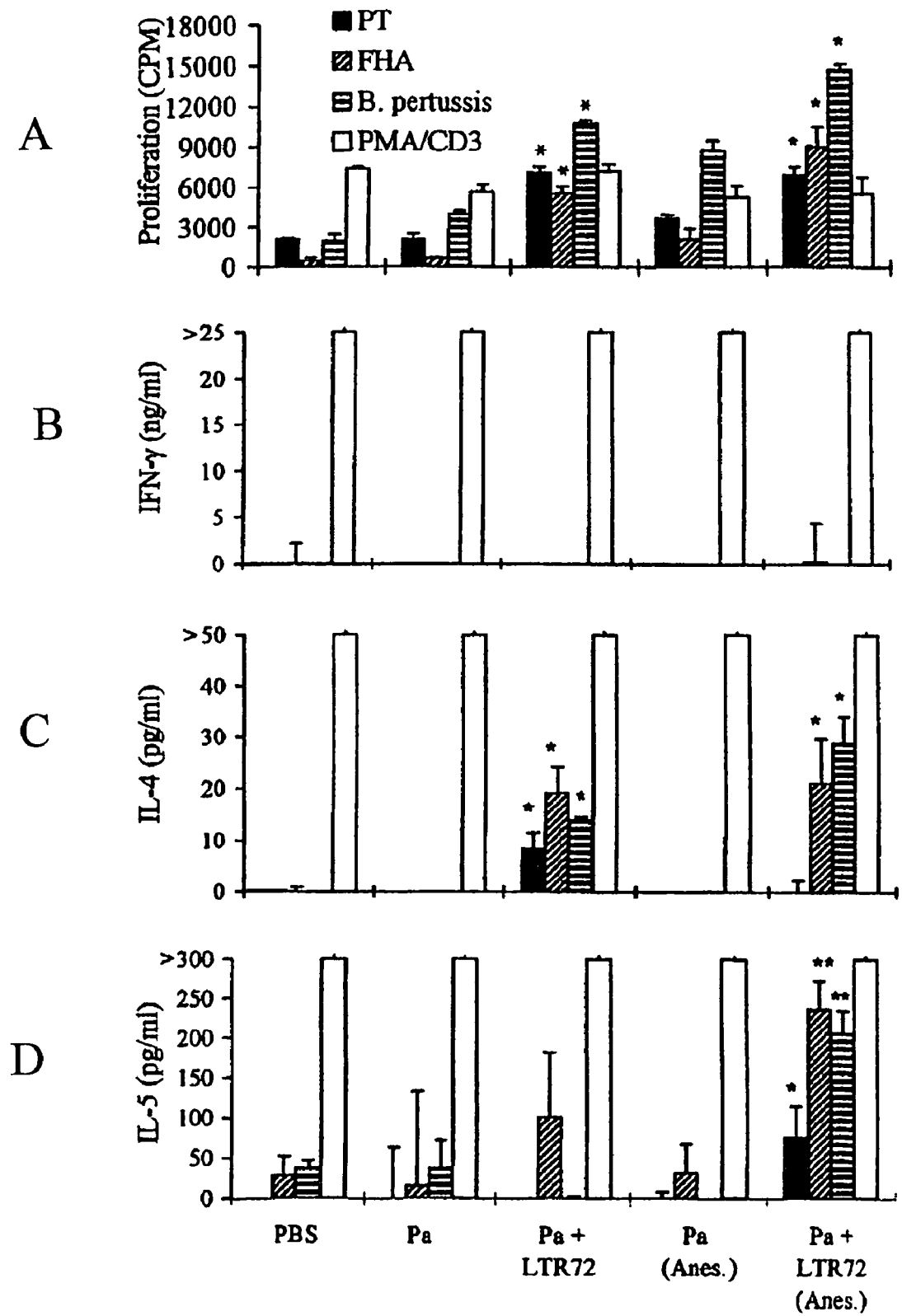
FIGS. 2A-2L show similar data for LT-R72 adjuvant, in (2A-2D) spleen (2E-2H) thoracic lymph node (2I-2L) superficial cervical lymph node. PMA/CD3 (no shading) was used as a positive control.
Figure 2:
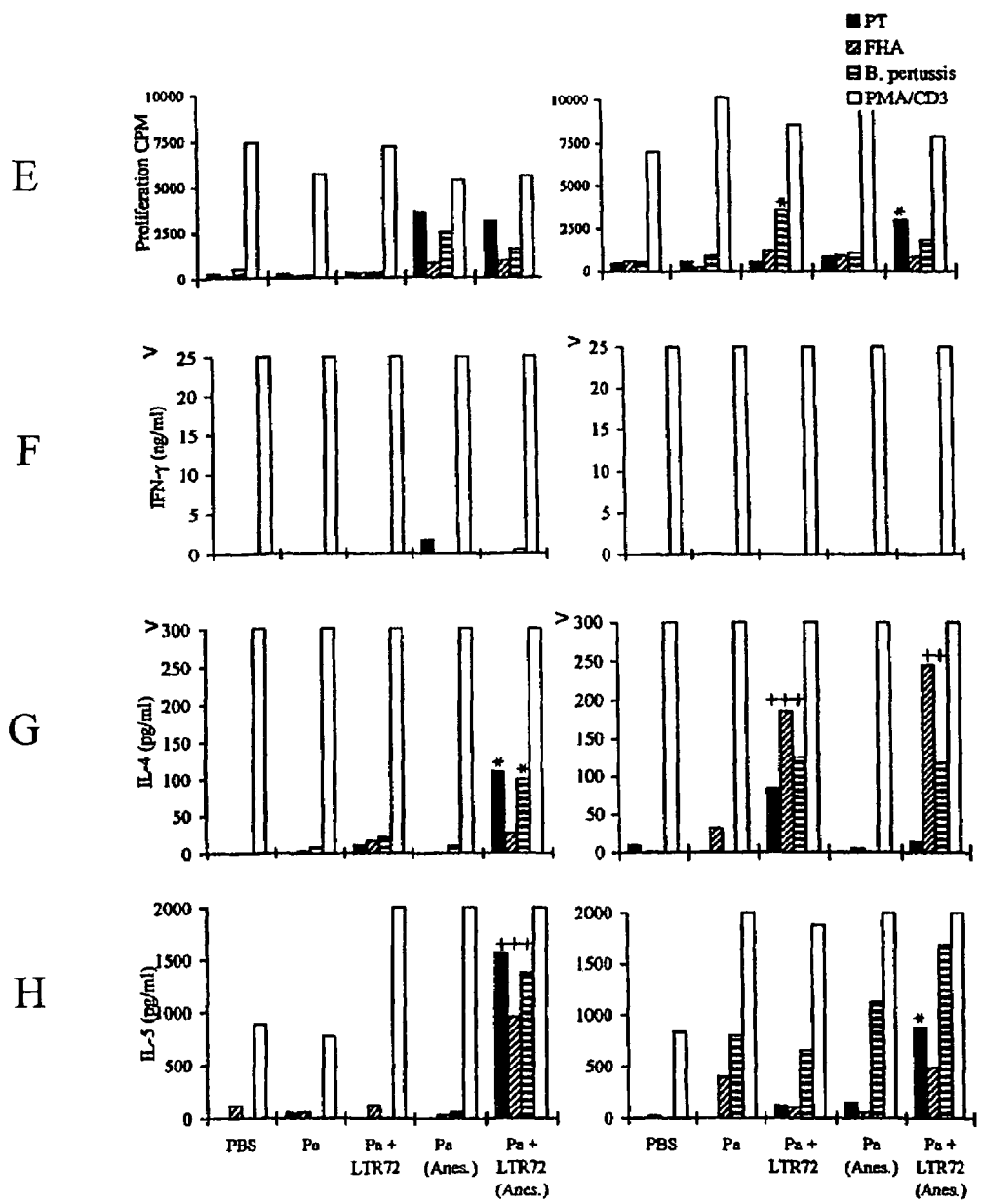
Figure 4:
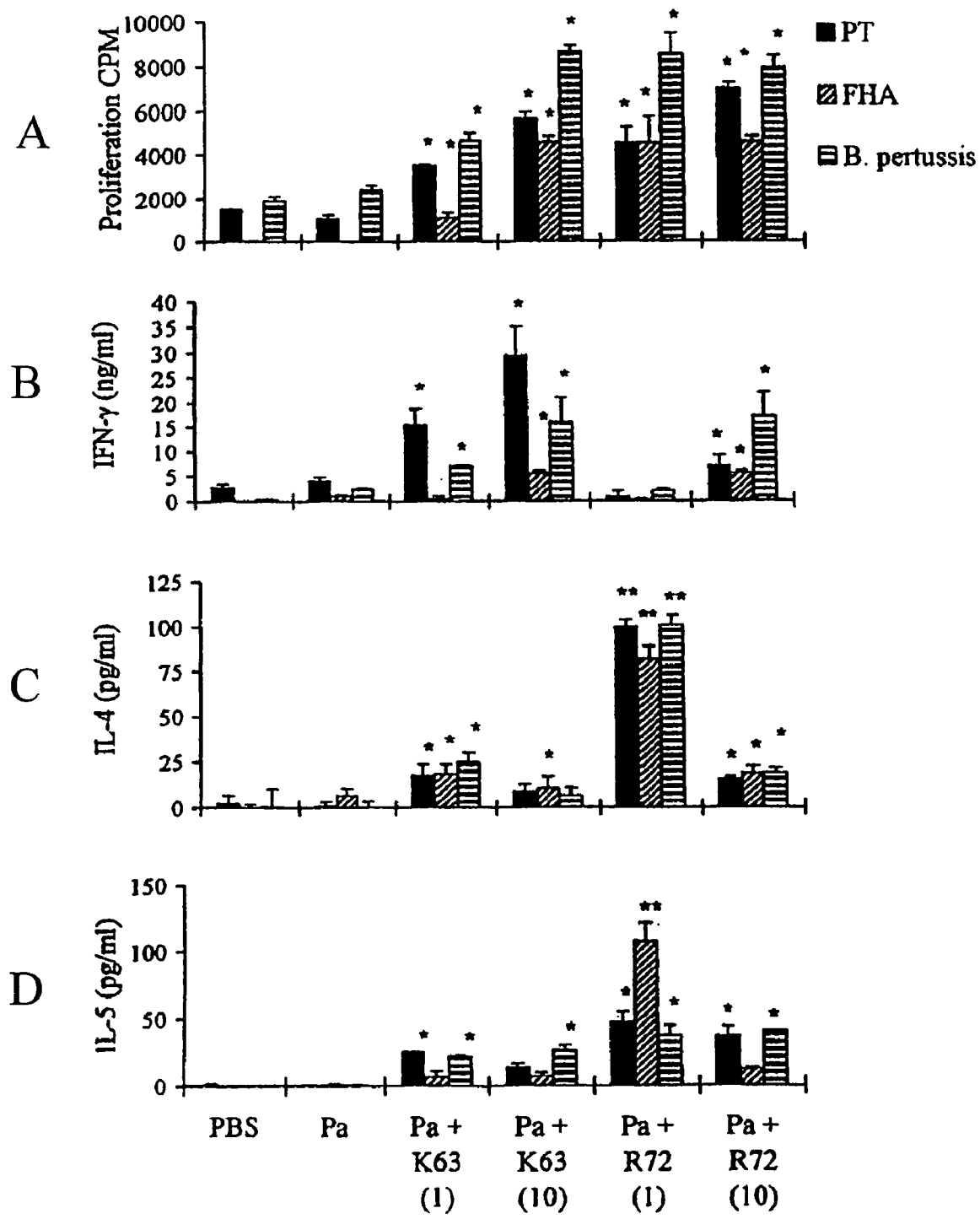
FIGS. 4A-4D show the effect of toxin dose on the adjuvant effect of the mutant LT adjuvants.

In all Figures in which it was calculated, statistical significance (Student's t test) versus Pa alone is indicated by either * ($P<0.05$) or ** ($P<0.01$).

MODES FOR CARRYING OUT THE INVENTION

Background Materials & Methods

Mice used in the following examples were female BALB/c mice, 6-8 weeks old, from Harlan UK and were housed according to the regulations of the Irish Department of Health.

T-cell responses Mice were immunized at 0 and 4 weeks. At 6 weeks, spleen, superior cervical lymph nodes and posterior mediastinal (thoracic) lymph nodes were removed and immune responses were evaluated. Spleen cells from individual mice or pooled lymph node cells ($2\times10^6$ cells/ml) from naive or immunized mice were cultured in triplicate in 8% FCS supplemented RPMI at 37 T with heat-killed (80° C. for 30 minutes), *B. pertussis* bacteria ($10^6$ or $10^7$ cells/ml), heat inactivated rPT (1-5 µg/ml), or FHA (1-5 µg/ml). Phorbal myristate acetate (PMA)+anti-mouse CD3 was used as a positive control; medium only was used as a negative control. In experiments using DTPa, responses were also tested against PRN, TT, or CRM197 (1-5 µg/ml). Supernatants were removed after 72 hours and the concentration of IFN-γ (indicative of Th1 response) and IL-4 & IL-5 (both indicative of Th2 response) were determined by immunoassay as described in reference 22. T-cell proliferation was assessed after 4 days of culture by $^3$H-thymidine uptake, also as described in reference 22. Results are expressed as mean counts per minute or mean cytokine concentration for the optimum concentration of antigen in assays performed in triplicate on individual spleen cells or pooled lymph node cells from four to five mice.

Antibody Assays

Levels of antigen-specific IgG in the serum of control and immunized mice were determined by ELISA. Purified antigens (FHA, PT, TT and DT; 1 µg/ml) were used to coat the ELISA plates. The plates were blocked with milk protein, then serially diluted serum samples were added, the bound antibody was detected by anti-mouse IgG (Fc-specific) alkaline-phosphatase conjugate. Antigen-specific IgA in lungs was detected by ELISA. Lungs were homogenized in 8% FCS supplemented RPMI containing 0.1 mM PMSF protease inhibitor. ELISA plates were coated with antigen as for the IgG assay and serially diluted lung homogenate was added. Bound antibody was detected with sheep anti-mouse IgA, followed by donkey-anti-sheep IgG alkaline phosphatase conjugate. Results are expressed as end point titres, calculated by regression of the straight part of a curve of optical density versus serum or lung homogenate dilution to a cut-off of 2 standard deviations above background control values for serum or lung homogenates from naive mice.

EXAMPLE 1

LT Mutants are Intranasal Adjuvants for Pa

The first vaccine (FIGS. 1A-1D) was adjuvanted with LT-K63 (10 µg/dose), whereas the second vaccine (FIGS. 2A-2L) was adjuvanted with LT-R72 (1 µg/dose). A control vaccine consisted of FHA+rPT only. The adjuvants were prepared as described in references 24 and 25.

Mice were immunized at 0 and 4 weeks either with the vaccine dose resuspended in 25 µl and applied to the external nares with a micropipette or, following light halothane anesthesia, with the vaccine dose resuspended in 50 µl and applied to the external nares with a micropipette. T-cell responses to killed B. pertussis, heat-inactivated PT and FHA were measured in spleen and thoracic and cervical lymph nodes at 6 weeks (FIGS. 1A-1D and 2A-2L).

1Strong T-cell proliferation and cytokine production was detected for the adjuvanted Pa vaccines. In contrast, spleens and local lymph nodes from mice intranasally immunized with the control failed to generate significant B. pertussis-specific T-cell responses. Positive responses to the polyclonal stimulus (PMA+anti-CD3) confirms that these T-cells were capable of responding in vitro.

FIGS. 3A-3D show that the mutant LT adjuvants also enhanced local and systemic antibody production following intranasal delivery of Pa. Immunization with the control generated weak and inconsistent anti-PT and anti-FHA serum IgG and lung IgA responses. In contrast, formulation of the same antigens with LT-R72 or LT-K63 resulted in consistently strong serum IgG and lung IgA specific for PT and FHA and also significantly enhanced IgA responses, especially when the vaccine was administered under anaesthesia.

The presence of the LT mutants thus resulted in better T-cell and antibody responses. They can enhance the protective efficacy of a nasally delivered Pa, and are therefore effective intranasal adjuvants for acellular vaccines.

EXAMPLE 2

Effect of Enzyme Activity and Toxin Dose on Adjuvanticity

The cytokine profiles obtained in Example 1 that the ADP-ribosylation activity of the toxins plays an important role in the modulation of the immune response. The K63 adjuvant, which is devoid of any toxic enzyme activity, enhanced the production of IL-4, IL-5, and IFN-γ, characteristic of a mixed Th1-Th2 (i.e. Th0) profile. In contrast, 1 µg of the R72 adjuvant, which retains partial toxic enzyme activity, appeared to selectively enhance Th2 cells.

In experiments that directly compared the adjuvanticity of the toxins in vivo, BALB/c mice were immunized with Pa formulated with 1 or 10 µg of LTK63 or LTR72 as adjuvant, and the resulting immune responses were assessed (FIGS. 4A-4D). Intranasal immunization with control Pa generated weak T-cell responses, whereas addition of 1 µg LTK63 enhanced proliferation, as well as IFN-γ and IL-5 production, by spleen cells and lymph nodes in response to FHA or killed B. pertussis. Increasing the dose to 10 µg LTK63 resulted in modest further enhancements of proliferation and IFN-γ production. 1.0 µg LTR72 selectively augmented Th2 responses, with elevated levels of antigen-induced IL-4 and IL-5 production compared with those observed with Pa alone. Wild-type LT (1.0 µg) also selectively enhanced IL-4 and IL-5 production, but the effect was not as dramatic as that observed with LTR72. Furthermore, the mice that received 1.0 µg LTR72 had significantly higher anti-FHA and anti-PT IgG and IgA antibody titres than those immunized using LTK63 or wild-type LT. Increasing the dose of LTR72 from 1.0 to 10 µg resulted in enhancement of IFN-γ levels and lower levels of IL-4 and IL-5.

Thus, the enzyme activity and the dose of the toxin appear to affect the cytokine profile of the antigen-specific T cells induced. The trace amounts of ADP-ribosylating activity present in low doses of LTR72 are sufficient to modulate the cytokine profile to Th2 and act as a potent adjuvant for antibody responses. Conversely, the adjuvant effect of LTK63, which is mediated by the binding effect of the AB complex, is pushed more toward the Th1 subtype. Furthermore, at higher doses of LTR72, the AB binding activity may outweigh the enzyme activity, resulting in enhancement of Th1 as well as Th2 cell induction.

EXAMPLE 3

Protection Against Pertussis Infection

Vaccine efficacy in human clinical trials has been correlated with the protection of immunized mice in the respiratory challenge model described in reference 22. This model was therefore used to assess intranasally delivered Pa formulated with the LT adjuvants, in order to predict human efficacy.

B. pertussis W28 phase I was grown under agitation conditions at 37° C. in Stainer-Scholte liquid medium. Bacteria from a 48 hour culture were resuspended at a concentration of approximately $2 \times 10^{10}$ cells/ml in physiological saline containing 1% casein. The challenge inoculum was administered to mice over a period of 15 minutes by means of a nebuliser, followed by rest in the chamber for a further 15 mins. Groups of 4 mice were sacrificed at 0, 3, 7, 10 and 14 days, and the number of viable B. pertussis in the lungs were assessed. Lungs were removed aseptically from infected mice and homogenized in 1 ml sterile physiological saline with 1% casein on ice. Aliquots of 100 µl undiluted or serially diluted homogenate from individual lungs were spotted in triplicate onto Bordet-Genou agar plates, and the number of colonies was assessed after 5 days incubation (FIG. 5).

The adjuvanted Pa formulations provided levels of protection significantly greater than those achieved with soluble antigens alone. The LT-K63 adjuvant generated marginally better protection than LT-R72. Nasal delivery of Pa with LT-R72 in 25 µl (no anaesthetic) gave marginally better protection than the same vaccine in 50 µl (with anaesthetic). Neither of these two differences was significant.

Figure 5A:
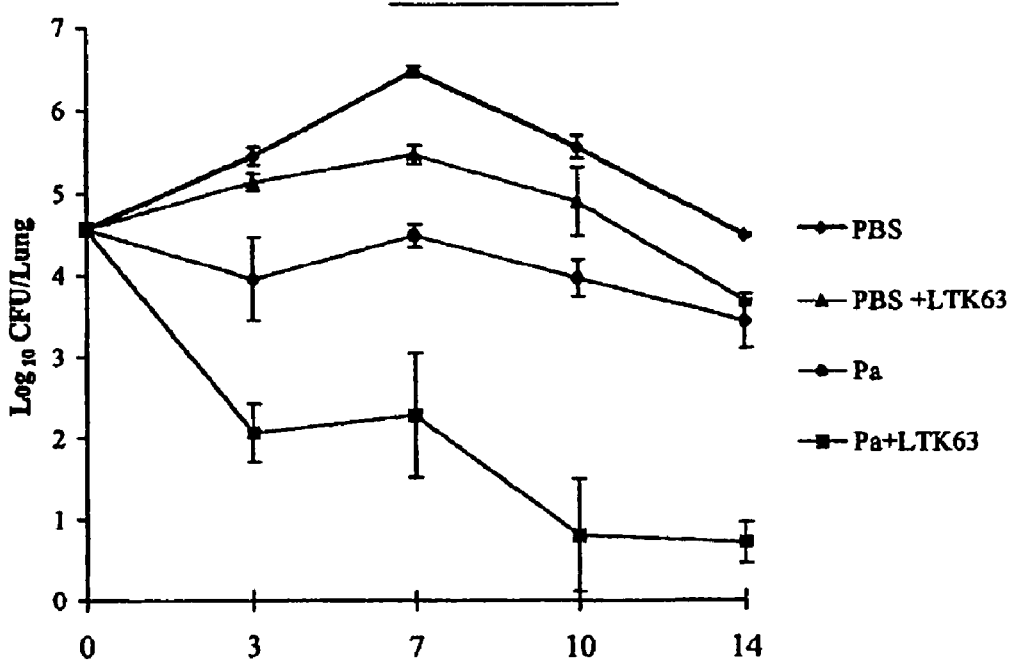
FIG. 5A shows results using LT-K63, and 5B shows results using LT-R72. Results are the mean viable *B. pertussis* for individual lungs from four mice per timepoint per experimental group.
Figure 5B:
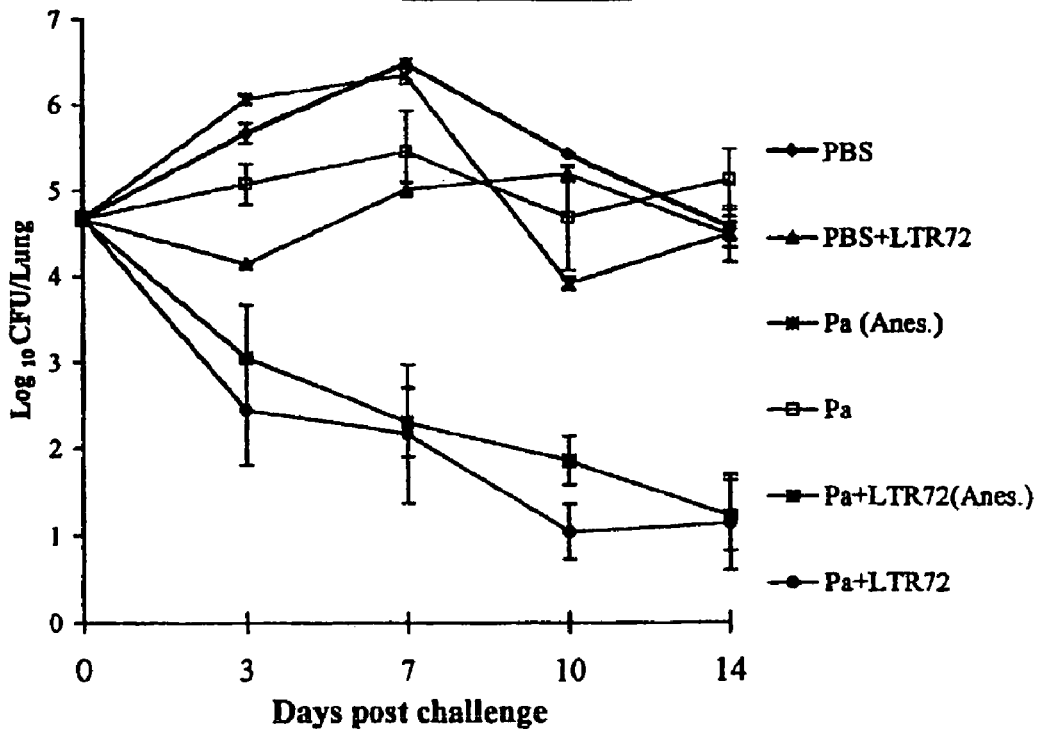
FIG. 5 shows the kinetics of *B. pertussis* clearance after immunization with the same vaccines as FIGS. 1 & 2.
Figure 6:
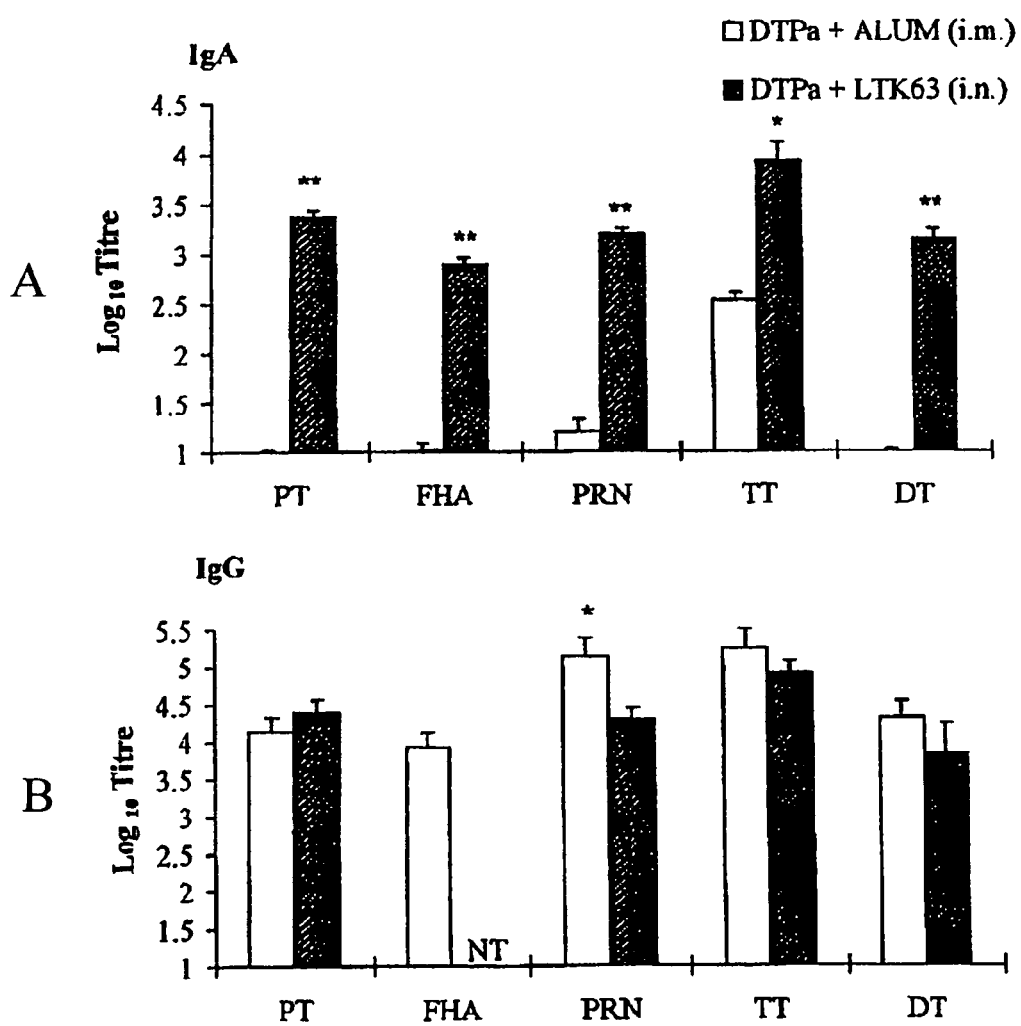
FIGS. 6A-6B show the IgA and IgG responses against the five antigens in a DTPa vaccine, comparing (i) alum adjuvant and intramuscular administration (empty bars) and (ii) LT-K63 adjuvant and intranasal administration (filled bars).
Figure 7:
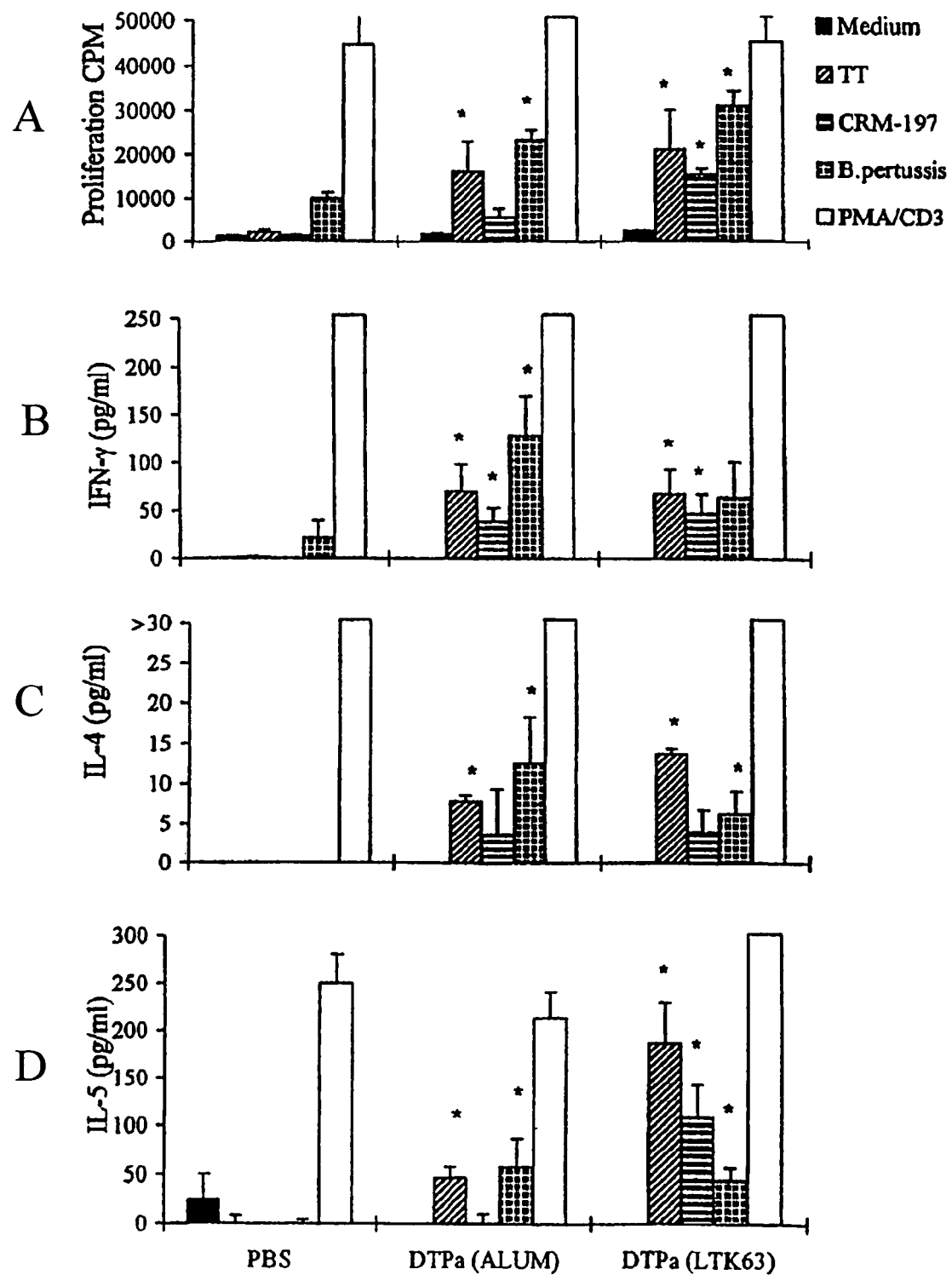
FIGS. 7A-7D compare T-cell responses for the same vaccines as shown in FIGS. 6A-6B.

The protection levels shown in FIG. 5 exceed those previously observed with a conventional parenterally delivered two component Pa (25 µg FHA+25 µg chemically-detoxified PT on alum [16,22]). Extrapolation of the correlation curve shows a better potency index, suggesting superior clinical efficacy in humans.

EXAMPLE 4

DTPa Efficacy Using LT-K63

Pertussis vaccines are usually administered intramuscularly to children in the form of atrivalent DTP combination on alum adjuvant. To assess the efficacy of intranasal vaccination, a DTPa vaccine was therefore adjuvanted with alum (300 µg/dose, 300 µl volume) for intramuscular administration, for direct comparison with the LT-K63-adjuvanted intranasal vaccine (10 µg adjuvant/dose, 40 µl volume). The Pa component of the vaccine included 5 µg rPT, 2.5 µg FHA and 2.5 µg pertactin; the T component was 10 µg tetanus toxoid; the D component was 10 µg CRM197.

The intranasal vaccine enhanced cellular and humoral immune responses to tetanus and diphtheria as well as pertussis antigens (FIGS. 6A-6B and 7A-7D). The levels of serum IgG using the intranasal vaccine were equivalent to those observed using the intramuscular vaccine, but the mucosal immunization advantageously enhanced local IgA responses.

Figure 8:
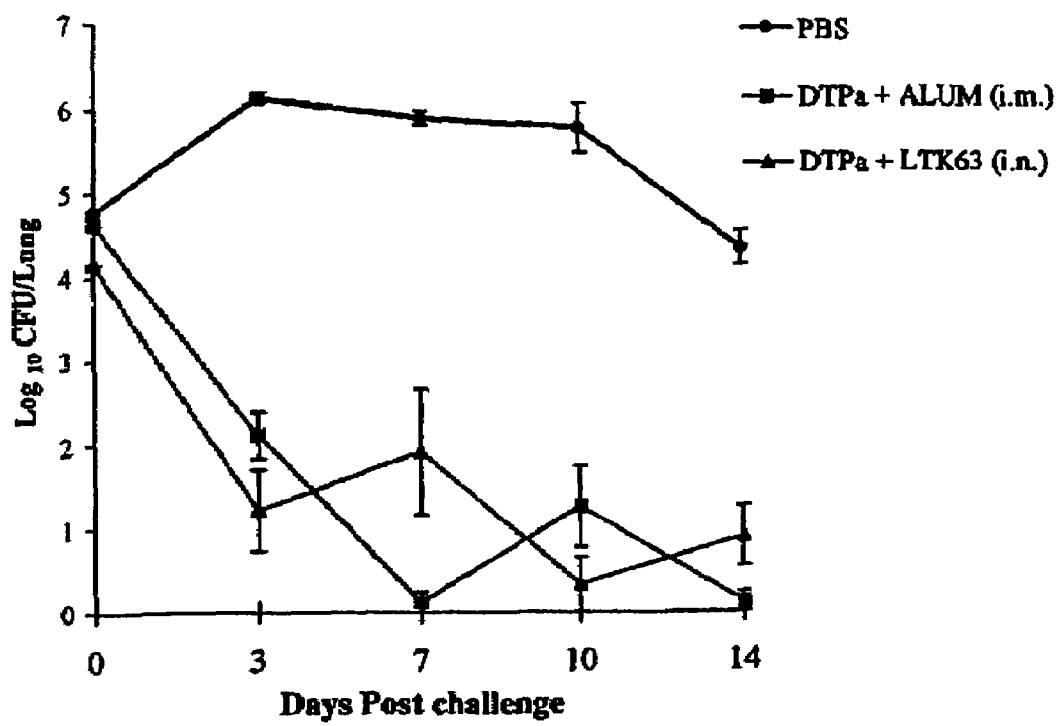
FIG. 8 shows the clearance kinetics of the vaccines of FIG. 6.

Significantly, the protective efficacy of the LT-K63-adjuvanted vaccine matched that of the "standard" alum-adjuvanted vaccine, although clearance kinetics varied slightly (FIG. 8). This is the first disclosure of a mucosally-delivered combined DTPa formulation that is capable of generating a level of protection against *B. pertussis* infection equivalent to that observed with the same antigens adsorbed on alum and administered parenterally.

EXAMPLE 5

Intramuscular Priming and Intranasal Booster

The DTPa vaccine was also used in a prime-boost experiment.

Two groups of 22 mice were immunized intramuscularly at 0 and 4 weeks with either DTPa on alum, or PBS (control). A further group of 22 mice was immunized intranasally at 0 and 4 weeks with the LT-K63-adjuvanted vaccine. Two further groups of 22 mice were immunized with the intramuscular alum formulation at week 0, and the intranasal formulation (with or without LT-K63 adjuvant) at week 4. (Table 1).

TABLE 1

| Group | Priming Dose | Boosting Dose |
|---|---|---|
| 1 | PBS | PBS |
| 2 | Intramuscular DTPa (alum) | Intramuscular DTPa (alum) |
| 3 | Intramuscular DTPa (alum) | Intramuscular DTPa (PBS) |
| 4 | Intramuscular DTPa (alum) | Intranasal DTPa (LT-K63) |
| 5 | Intranasal DTPa (LT-K63) | Intranasal DTPa (LT-K63) |

Five mice from each group were sacrificed at week 6, and serum, lungs and spleen cells were measured for immune responses. The remaining mice were subjected to the infection model. One mouse from each group on day 0 and four mice from each group on days 3, 7, 10 and 14 were sacrificed, and their CFU-counts were measured from their lungs.

Figure 9:
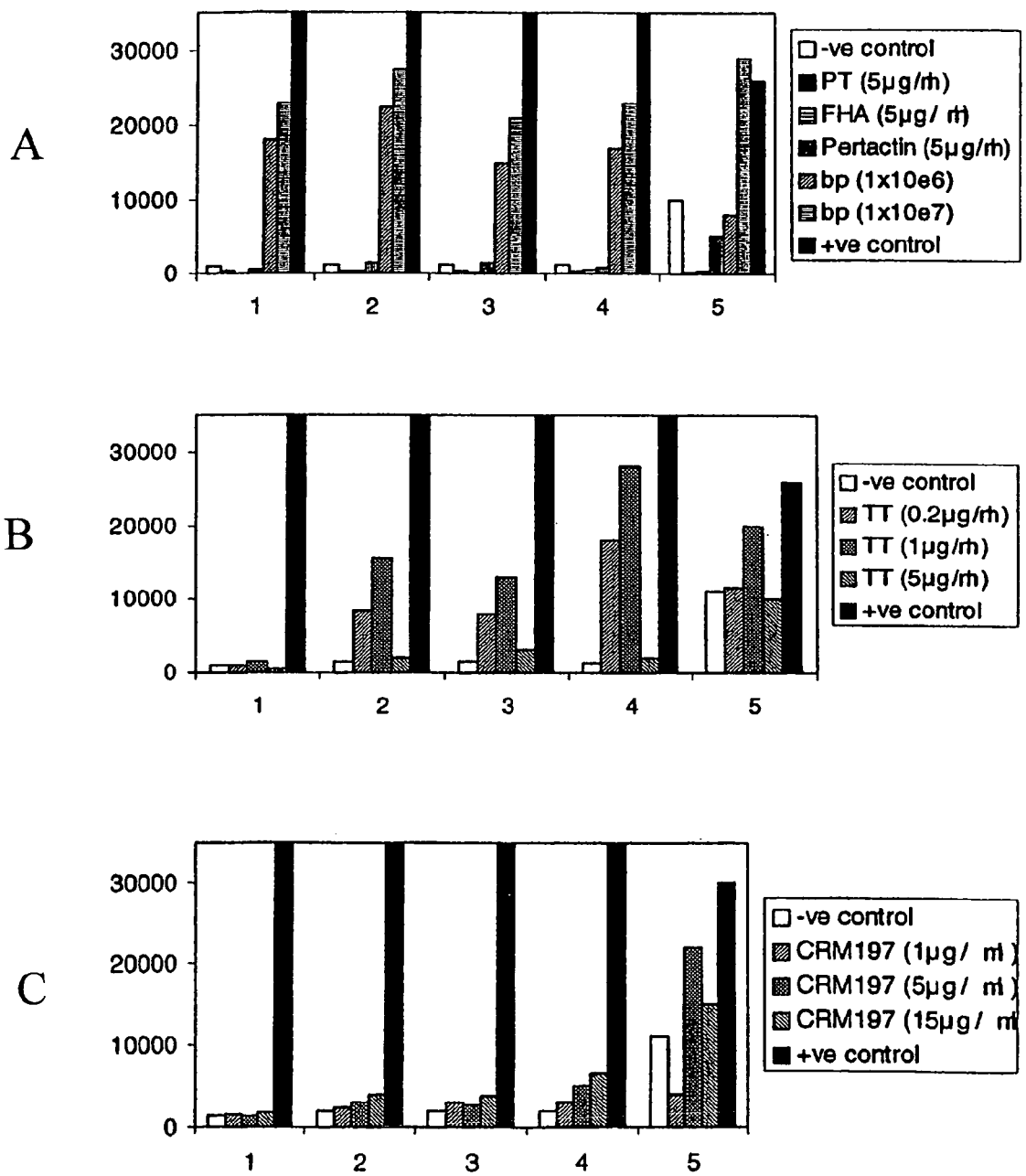
FIGS. 9A-9C show T-cell proliferation (measured as $^3$H-CPM) against the D (9C), T (9B) and Pa (9A) components of DTPa vaccines administered using 5 different prime and boost regimens.

T-cell proliferation (FIGS. 9A-9C) was weak for all groups for spleen cells stimulated with the pertussis antigens in vitro. The cells did, however, proliferate in response to the positive control (PMA+CD3). Proliferation responses to tetanus toxoid in vitro were significantly stronger in intranasally-boosted mice (after intramuscular priming) when LT-K63 was used as adjuvant. The strongest in vitro proliferation against the diphtheria component was seen in the mice immunized intranasally twice.

Figure 10:
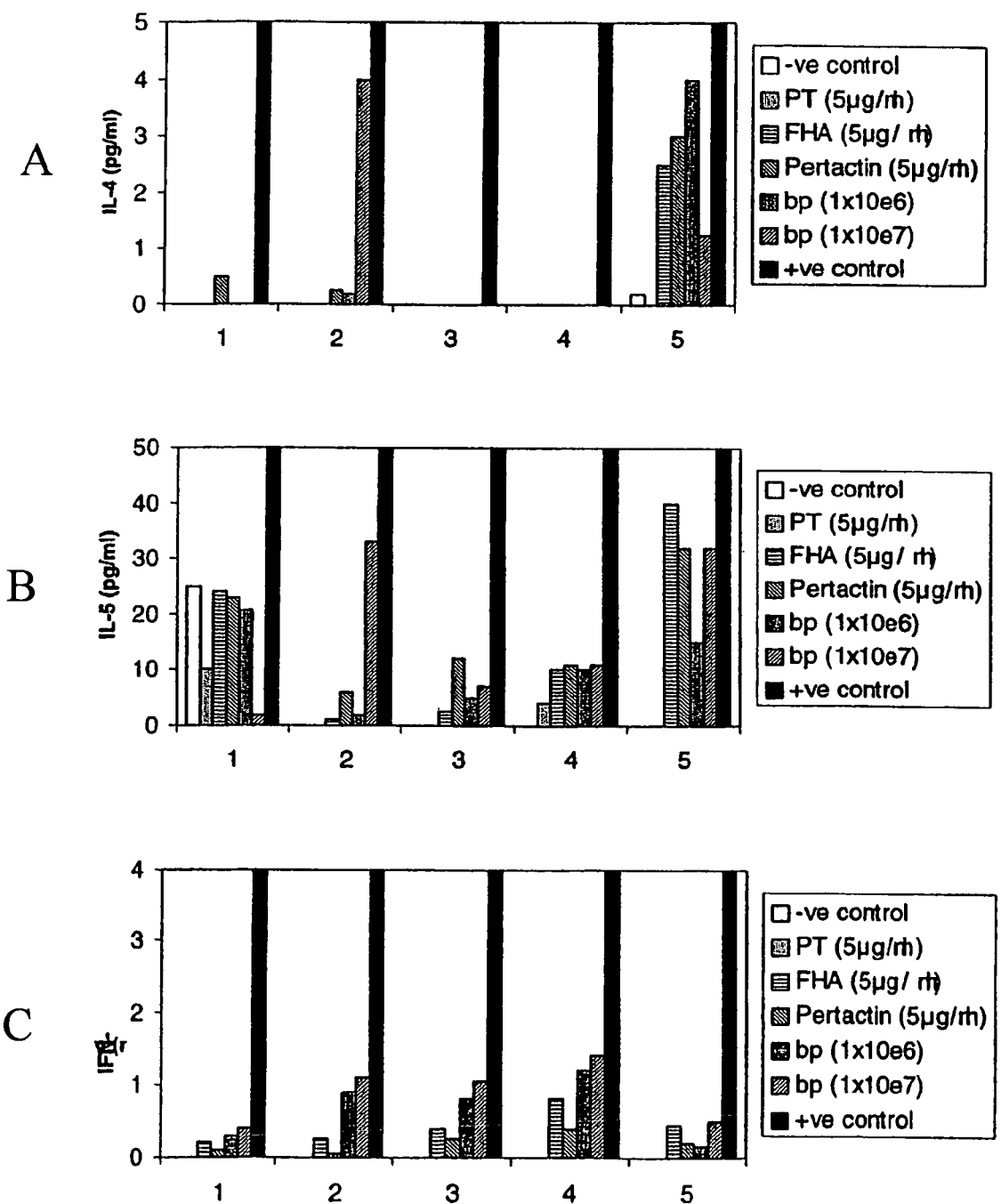
FIGS. 10A-10C show the T-cell cytokine responses against the Pa component of the vaccines of FIGS. 9A-9C.

Cytokine responses to pertussis antigens (FIGS. 10A-10C) showed both IL-5 and IFN-γ production in all groups, indicating priming of both Th1 and Th2 populations in vivo. IL-4 production was limited to groups immunized in the same way both times. Priming and boosting with the intranasal LT-K63 formulation seems to give a stronger Th2 response (higher IL-4 and IL-5) than the groups primed intramuscularly.

Figure 11:
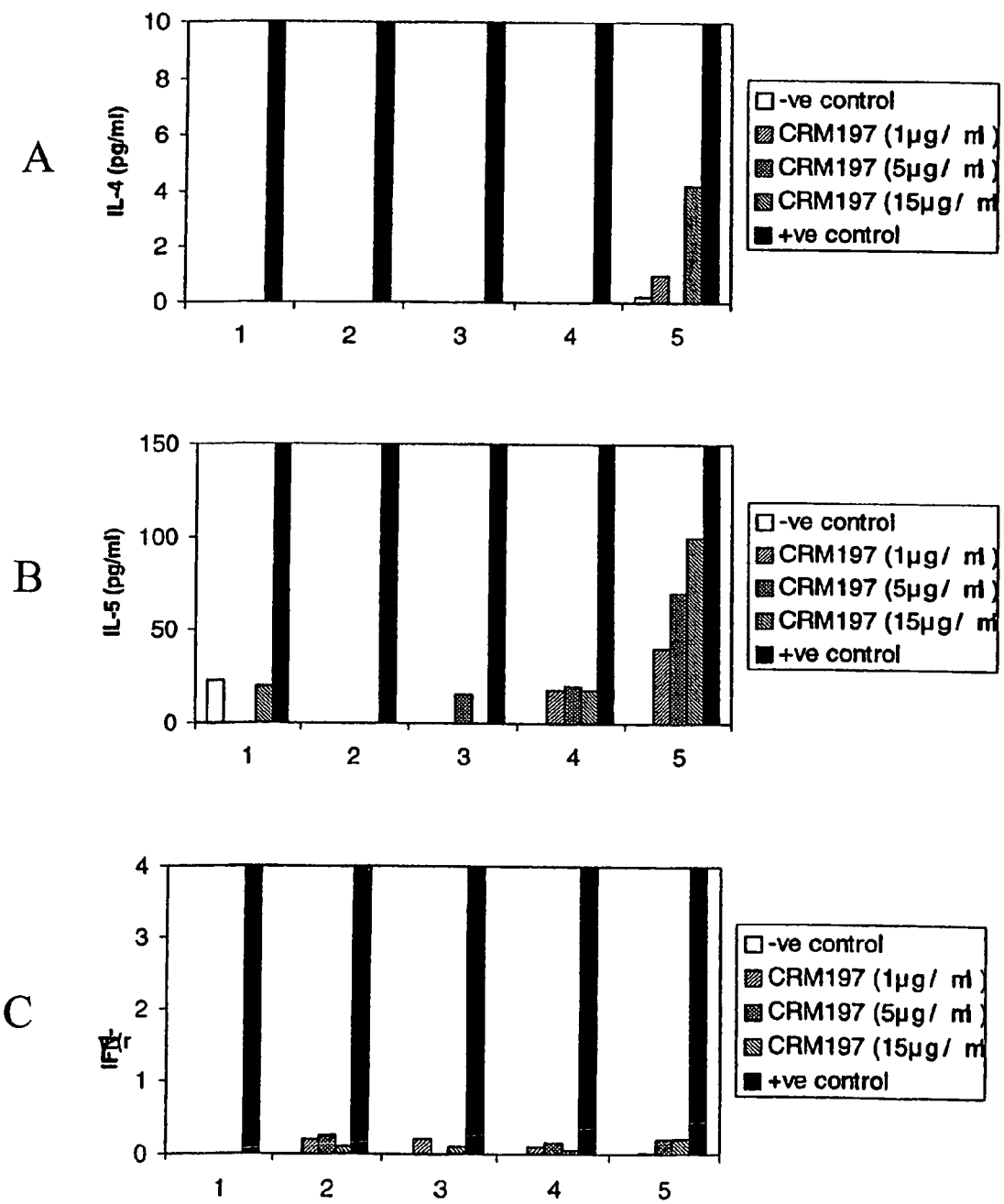
FIGS. 11A-11C show the T-cell cytokine responses against the D component of the vaccines of FIGS. 9A-9C.
Figure 12:
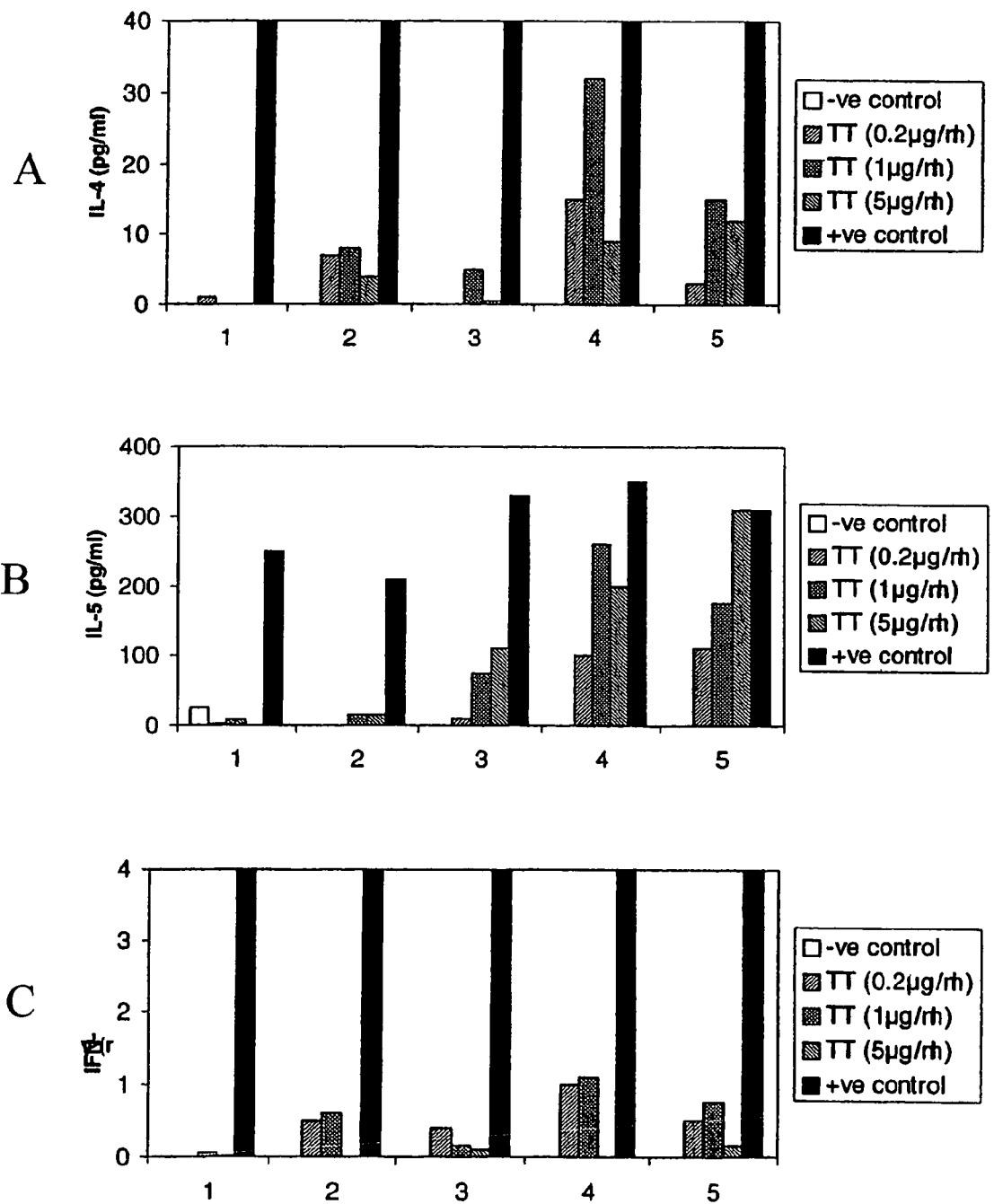
FIGS. 12A-12C show the T-cell cytokine responses against the T component of the vaccines of FIGS. 9A-9C.

Cytokine responses against the diphtheria antigen (FIGS. 11A-11C) were restricted to IL-4 and IL-5, with little or no IFN-γ detected for any group. Intranasal boosting with DTPa thus results in the priming of Th2 cells in vivo. The strongest Th2 response was generated from the mice immunized intranasally twice with the LT-K63 adjuvant. In contrast, two intramuscular injections gave no detectable IL-4 or IL-5 responses in the spleen, nor any IFN-γ.

Figure 14:
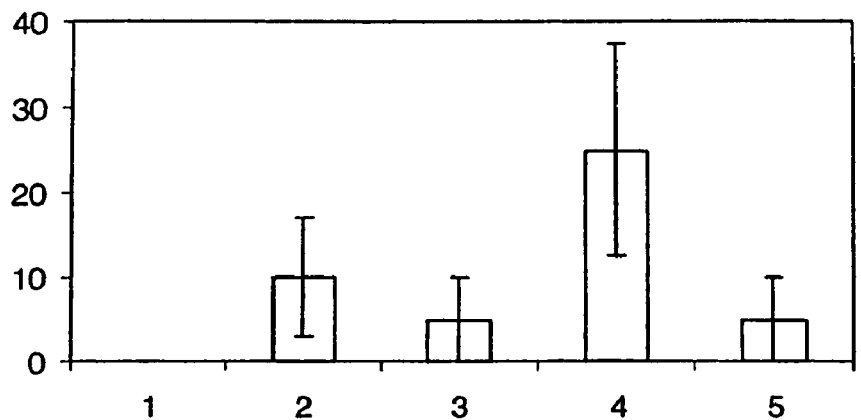
FIG. 14 shows the functionally important anti-DT neutralizing antibodies.

Analysis of functionally important anti-DT neutralizing antibodies in murine sera (FIG. 14) demonstrated that intramuscular priming and intranasal boosting using LT-K63 resulted in the highest levels.

Figure 15:
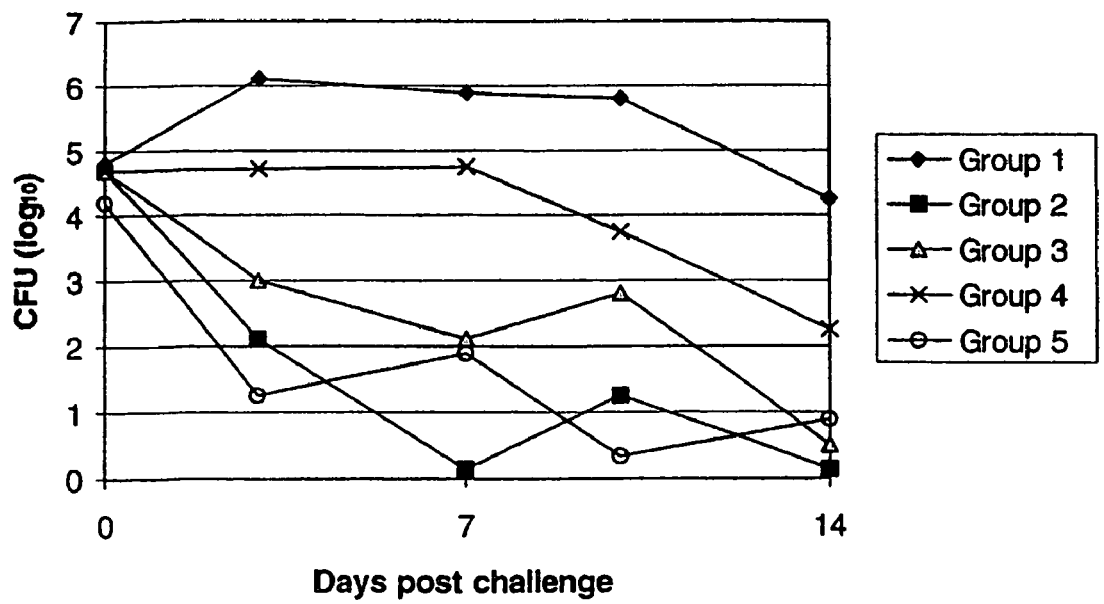
FIG. 15 shows clearance kinetics for the five regimens.

The protection model showed that similar levels of protection was obtained in the dual-intranasal and dual-intramuscular immunizations. Whilst the kinetics of the clearance curves (FIG. 15) vary, *B. pertussis* was effectively cleared in both cases, with CFU counts below 1 ($\log_{10}$) 14 days after challenge. Most adults today have received an intramuscular pertussis vaccination. This is represented by the intramuscular priming in this example. The data show that intranasal boosting with LT-K63 adjuvant is an effective method of vaccination.

This example also shows that LT-K63 is a very effective adjuvant for the delivery of 1X CRM197. Intranasal enhancement against this antigen has been reported using chitosan, although this required three immunizations for modest IgA and T-cell responses. In contrast, LT-K63 was able to induce strong IgG, IgA, IL-4 and IL-5 responses after just two intranasal immunizations. Similar levels of anti-DT neutralizing antibodies were also generated as with chitosan.

it will be understood that the invention is described above by way of example only and modifications may be made whilst remaining within the scope and spirit of the invention.

REFERENCES

The Contents of Which are Incorporated Herein in Full by Reference

1. Center for Disease Control and Prevention (1997) Morbid. Mortal. Weekly Rep. 46:RRI-RR25
2. Rappuoli (1997) *Nature Medicine* 3:374-376
3. Walker (1994) *Vaccine* 12:387-400
4. Cahill et al. (1995) *Vaccine* 13:455-462
5. Cahill et al. (1993) *FEMS Microbiology Letters* 107:211-216
6. Jones et al. (1996) *Infect. Immun.* 64:489-494
7. Shahin et al. (1992) *Infect. Immun.* 60:1482-1488
8. Shahin et al. (1995) *Infect. Immun.* 63:1195-1200
9. Guzman et al. (1993) *Infect. Immun.* 61:573-579
10. Del Guidice et al. (1998) *Molecular Aspects of Medicine* 19:1-70
11. W093/13202
12. W098/18298
13. Park et al. (2000) *Exp. Mol. Med.* 32:72-78

14. Fontana et al. (1995) *Infect. Immun.* 63:2356-2360
15. Almeida & Alpar (1996) *J. Drug Targeting* 3:455-467
16. Gustafsson et al. (1996) *N. Engl. J. Med.* 334:349
17. Rappuoli et al. (1991) *TIBTECH* 9:232-238
18. Wassilak & Orenstein, Chapter 4 of Vaccines (eds. Plotkin & Mortimer), 1988.
19. W093/24148
20. Hauser et al. (1998) *Dev Biol Stand* 95:251-255
21. Donnelly et al. (1997) *Annu Rev Immunol* 15:617-648
22. Mills et al. (1998) *Infect. Immun.* 66:2594-2602
23. Podda et al. (1991) *Vaccine* 9:741-745
24. Douce et al. (1995) *PNAS USA* 92:1644-1648
25. Giulani et al. (1998) *J. Exp. Med.* 187:1-10

What is claimed is:

1. An intranasal vaccine comprising:
   a diphtheria toxoid, a tetanus toxoid, and an acellular pertussis antigen (DTPa) comprising detoxified pertussis holotoxin; and
   a detoxified *E. coli* heat labile toxin, wherein the detoxified *E. coli* heat labile toxin is LT-K63 or LT-R72.

2. The intranasal vaccine of claim 1, wherein the acellular pertussis antigen comprises filamentous haemagglutinin.

3. The intranasal vaccine of claim 2, wherein the acellular pertussis antigen further comprises pertactin.

4. The intranasal vaccine of claim 2, wherein the detoxified pertussis holotoxin is 9K/129G double mutant.

5. The intranasal vaccine of claim 1, wherein the diphtheria toxoid is CRM197.

6. The intranasal vaccine of claim 1 further comprising at least one additional non-DTP antigen which does not diminish the immune response against said DTPa.

7. A method of generating an immune response against diphtheria, tetanus, and whooping cough in a patient comprising intranasally administering to the patient the vaccine of claim 1.

8. The method of claim 7, wherein the patient is a child.

9. The method of claim 7, wherein the intranasal administration is performed at least twice.

* * * * *